United States Patent
Lei et al.

(10) Patent No.: US 11,918,253 B1
(45) Date of Patent: Mar. 5, 2024

(54) ACTIVE VARIABLE STIFFNESS CLAMPING DEVICE FOR PELVIC FRACTURE REDUCTION ROBOT

(71) Applicant: Shanghai University, Shanghai (CN)

(72) Inventors: Jingtao Lei, Shanghai (CN); Xinyi Chen, Shanghai (CN); Shenyang Cai, Shanghai (CN)

(73) Assignee: Shanghai University, Shanghai (CN)

( * ) Notice: Subject to any disclaimer, the term of this patent is extended or adjusted under 35 U.S.C. 154(b) by 0 days.

(21) Appl. No.: 18/111,700

(22) Filed: Feb. 20, 2023

(30) Foreign Application Priority Data

Nov. 4, 2022 (CN) .......................... 202211378153.0

(51) Int. Cl.
*A61B 17/66* (2006.01)
*A61B 17/64* (2006.01)
*A61B 17/00* (2006.01)

(52) U.S. Cl.
CPC .......... *A61B 17/66* (2013.01); *A61B 17/6408* (2013.01); *A61B 17/6416* (2013.01); *A61B 17/6433* (2013.01); *A61B 2017/00398* (2013.01)

(58) Field of Classification Search
CPC . A61B 17/66; A61B 17/6408; A61B 17/6416; A61B 17/6433; A61B 2017/00398
USPC ........................................ 606/54, 56, 57, 59
See application file for complete search history.

(56) References Cited

U.S. PATENT DOCUMENTS

| | | | | |
|---|---|---|---|---|
| 5,451,226 A | * | 9/1995 | Pfeil ................... | A61B 17/6458 606/53 |
| 2015/0119886 A1 | * | 4/2015 | Milella, Jr. ........ | A61B 17/6466 606/59 |
| 2016/0038184 A1 | * | 2/2016 | Erickson ............ | A61B 17/6425 606/59 |
| 2018/0256214 A1 | * | 9/2018 | Dejardin ............ | A61B 17/1703 |
| 2019/0274665 A1 | * | 9/2019 | Garcia ................. | A61B 90/50 |
| 2019/0336171 A1 | * | 11/2019 | Lavi ..................... | A61B 17/66 |
| 2023/0091158 A1 | * | 3/2023 | Starr .................... | A61B 17/88 606/56 |

FOREIGN PATENT DOCUMENTS

FR 3081317 A1 * 11/2019 ....... A61B 17/00234

* cited by examiner

*Primary Examiner* — Tessa M Matthews
*Assistant Examiner* — David C Comstock
(74) *Attorney, Agent, or Firm* — The Dobrusin Law Firm, P.C.

(57) ABSTRACT

An active variable stiffness clamping device for pelvic fracture reduction robot, belonging to the technical field of medical robots. The clamping device includes an affected side adjusting support module and a healthy side fixing module which are in fit with each other. The affected side adjusting support module is provided with a pair of electric pin rod connector modules connected to the affected side adjusting support module. The healthy side fixing module includes a healthy side bed clamp seat, the healthy side bed clamp seat is provided with a healthy side support rod, the healthy side support rod is provided with a healthy side spherical hinge base, and the healthy side spherical hinge base is provided with a pair of healthy side fixers which are in clearance fit with each other.

11 Claims, 5 Drawing Sheets

ACTIVE VARIABLE STIFFNESS CLAMPING DEVICE FOR PELVIC FRACTURE REDUCTION ROBOT

CROSS-REFERENCE TO RELATED APPLICATION

This patent application claims the benefit and priority of Chinese Patent Application No. 202211378153.0, filed with the China National Intellectual Property Administration on Nov. 4, 2022, the disclosure of which is incorporated by reference herein in its entirety as part of the present application.

TECHNICAL FIELD

The present disclosure belongs to the technical field of medical robots, and in particular relates to an active variable stiffness clamping device for pelvic fracture reduction robot.

BACKGROUND

Pelvic fracture is one of the most challenging fractures in traumatic orthopedics clinic. Currently, clinical reduction is operated manually by doctors, and the doctors need to hold and maintain the reduction state during operation. Due to the complex structure of the pelvis, multiple times of x-ray are often required to check the reduction effect, and the reduction accuracy depends on the clinical experience of doctors. With the development of robot technology, the robot, instead of conventional operation, has the advantages of minimally invasive, high surgical precision, fast postoperative recovery, low labor intensity of doctors, and less radiation to both doctors and patients.

Robot-assisted pelvic fracture reduction is suitable for unstable pelvic fracture types. According to the Tile subtype of the fracture, the type B or type C fracture is suitable for robot surgery. Before the operation, the clamping device is required to fix the injured pelvis and the robot. (1) As the space between the surgical robot and the patient is very small, the structure of the clamping device should be very compact. (2) Due to the pulling of the soft tissues around the injured pelvis, the reduction force is usually as high as 500 N, so the clamping device is easy to deform, resulting in deformation and uneven stress, which affects the reduction accuracy of the robot. (3) Due to the different anatomical parameters of the pelvis of different patients, the clamping device should be easily adjustable to suit the needs of different patients. Therefore, the clamping device should not only be compact in structure and satisfy the requirements of strength and stiffness, but also should be able to have active variable stiffness during operation and be applicable to the requirements of large reduction force during operation. At present, there are no reports on the variable stiffness clamping devices for pelvic fracture reduction robot.

SUMMARY

To solve the technical problem above, the present disclosure provides an active variable stiffness clamping device for pelvic fracture reduction robot, which can stably clamp personalized pelvis and fracture types of different patients and improve the operation accuracy of the pelvic fracture reduction robot.

Based on the objective above, the present disclosure is achieved through the following technical solutions:

An active variable stiffness clamping device for pelvic fracture reduction robot includes an affected side adjusting support module and a healthy side fixing module, which are in fit with each other. The affected side adjusting support module is provided with a pair of electric pin rod connector modules connected to the affected side adjusting support module. The healthy side fixing module includes a healthy side bed clamp seat, the healthy side bed clamp seat is provided with a healthy side support rod, the healthy side support rod is provided with a healthy side spherical hinge base, and the healthy side spherical hinge base is provided with a pair of healthy side fixers which are in clearance fit with each other.

Preferably, the affected side adjusting support module includes an affected side spherical hinge base. The affected side spherical hinge base is provided with a butt joint which may be in rapid butt-joint with and locked with the tail end of a pelvic fracture robot. The affected side spherical hinge base is provided with an affected side cross rod and an affected side spherical hinge cross rod which are in clearance fit with each other. The affected side cross rod is fixedly connected to the affected side spherical hinge base, and the affected side spherical hinge cross rod is connected to the affected side spherical hinge base by an affected side adjuster.

Preferably, the affected side adjuster includes an affected side spherical hinge hole formed in the affected side spherical hinge base, the affected side spherical hinge hole is in fit with an affected side spherical hinge arranged at the end part of the affected side spherical hinge cross rod. The affected side spherical hinge base is provided with an affected side spherical hinge cover plate, and an affected side spherical hinge stopper in fit with the affected side spherical hinge cross rod is nested in the affected side spherical hinge cover plate. The affected side spherical hinge base is provided with an affected side spherical hinge stop pin, and the affected side spherical hinge stop pin is in fit with the affected side spherical hinge through an affected side limit hole which is formed in the affected side spherical hinge base to communicate with the affected side spherical hinge hole. The affected side adjusting support module can improve the flexibility of the clamping device by adjusting an angle between the affected side spherical hinge cross rod and the affected side spherical hinge base.

Preferably, the electric pin rod connector module includes a cross rod clamping assembly respectively connected to the affected side cross rod and the affected side spherical hinge cross rod. A pin clamping assembly is connected to the cross rod clamping assembly by a gasket stud, the gasket stud is nested in the cross rod clamping assembly to be rotatably connected to the cross rod clamping assembly. The pin clamping assembly includes a first-stage cylinder connected to the gasket stud, the top end of the first-stage cylinder is provided with an elastic collet, the elastic collet is provided with a nut threaded to the elastic collet. The elastic collet includes a collet sleeve arranged at the top end of the first-stage cylinder, elastic sheets which are in clearance fit with one another are uniformly distributed on the top end of the collet sleeve. One end of the elastic sheet is connected to the collet sleeve, and the other end of the elastic sheet inclines towards the axis of the collet sleeve. The cross rod clamping assembly may be rotationally adjusted around the axis of the gasket stud, and is connected to the affected side cross rod or the affected side spherical hinge cross rod by screwing the nut.

Preferably, a second-stage cylinder in clearance fit with the first-stage cylinder is nested in the first-stage cylinder, an inner cylinder holder is nested in the second-stage cylinder, the inner cylinder holder is in fit with a straight groove in the first-stage cylinder; and a third-stage cylinder in clearance fit with the first-stage cylinder is nested in the second-stage cylinder.

Preferably, the second-stage cylinder is provided with a second-stage adjusting boss, the second-stage adjusting boss is in fit with a first-stage spiral hole on the first-stage cylinder. The first-stage cylinder is provided with a gear motor, the movable end of the gear motor is provided with a gear, the gear is meshed with adjusting gear teeth arranged on the second-stage cylinder, and the adjusting gear teeth are in clearance fit with the inner surface of the first-stage cylinder. The electric pin rod connector module is driven by the gear motor to achieve the synchronous expansion and contraction of the second-stage cylinder and the third-stage cylinder, and thus the stiffness of the clamping device may be actively regulated and controlled during operation.

Preferably, the second-stage cylinder is provided with a second-stage spiral hole, the second-stage spiral hole is in fit with a third-stage adjusting boss arranged on the third-stage cylinder. An affected side pin in clearance fit with the second-stage cylinder and the third-stage cylinder is nested in the first-stage cylinder; the affected side pin is in running fit with a ball bushing nested in the third-stage cylinder, and the top end of the affected side pin is in fit with the elastic collet. An inner cylinder straight groove in fit with the third-stage adjusting boss is arranged on the inner cylinder holder. The first-stage cylinder is provided with a gearbox casing in fit with the gear; the first-stage spiral hole and the second-stage spiral hole are opposite in spiral directions. The pin clamping assembly employs the gear motor to drive the gear to rotate, thus driving a second-stage sleeve and a third-stage sleeve to axially move along the affected side pin. The second-stage sleeve and the third-sleeve sleeve are configured to improve the stiffness of the affected side pin when extending out, thus achieving the active regulation of the stiffness of the clamping device under the action of large reduction force during operation.

Preferably, the healthy side fixers each include a healthy side spherical hinge cross rod hinged to a healthy side spherical hinge base, the healthy side spherical hinge cross rod is provided with a pin rod connector adjustably connected to the healthy side spherical hinge cross rod, and the pin rod connector is provided with a healthy side pin adjustably connected to the pin rod connector.

Preferably, the healthy side bed clamp seat is provided with a healthy side support rod rotary knob in fit with the healthy side support rod, the healthy side bed clamp seat is provided with a healthy side bed clamp rotary knob, the healthy side bed clamp rotary knob is in fit with a healthy side bed clamp groove arranged on the healthy side bed clamp seat through a healthy side bed clamp gasket.

Preferably, one side, away from the healthy side spherical hinge cross rod, of the healthy side spherical hinge base is provided with a healthy side spherical hinge base fixing rotary knob in fit with the healthy side support rod, one side, close to the healthy side spherical hinge cross rod, of the healthy side spherical hinge base is provided with a healthy side spherical hinge cover plate in fit with the healthy side spherical hinge cross rod. The healthy side spherical hinge base is provided with a healthy side spherical hinge stop pin in fit with the healthy side spherical hinge cross rod, the healthy side spherical hinge stop pin is in fit with a healthy side spherical hinge arranged at the end part of the healthy side spherical hinge cross rod through a healthy side limit hole formed in the healthy side spherical hinge base, the healthy side spherical hinge is in fit with the healthy side spherical hinge hole arranged on the healthy side spherical hinge base, and the healthy side spherical hinge hole is in fit with the healthy side spherical hinge cover plate. The healthy side support rod is connected to the healthy side bed clamp seat and is compressed and fixed by the healthy side support rod rotary knob. The healthy side spherical hinge base is fixed to the healthy side support after being regulated up and down through the loosening and clamping of two healthy side spherical hinge fixing rotary knobs. The healthy side spherical hinge stop pin has the similar structural function as the affected side spherical hinge stop pin, and is configured to adjust a stopper in the healthy side spherical hinge base.

Compared with the prior art, the present disclosure has the beneficial effects as follows:

The clamping device disclosed by the present disclosure can adapt to the pins placed in the pelvis in different spatial positions according to the pelvic sizes and fracture types of different patients, can achieve the active regulation and control of the stiffness of the clamping device under the action of large reduction force during operation, and has remarkable advantages of compact structure, flexible adjustment, active variable stiffness, stable clamping, and convenient assembly and disassembly.

The clamping device disclosed by the present disclosure is configured to fix the affected side and the healthy side of the pelvis. The healthy side fixing module is configured to fix the healthy side part of the pelvis, which is liftable and rotatable to achieve adjustment in multiple directions, thus adapting to the pins placed in the pelvis in different spatial positions according to the personalized pelvic structures and fracture types of different patients, and achieving the stable clamping of the injured pelvis. In the electric pin rod connector module, the second-stage cylinder and the third-stage cylinder are driven by the gear motor to move in an axial direction of the affected side pin, thus achieving active regulation of the stiffness of the clamping device under the action of large reduction force during operation, reducing non-uniform deformation of the clamping device during operation, improving the strain and stress distribution states under the action of large reduction force during operation, and facilitating to improve the operation accuracy the pelvic fracture reduction robot. The affected side spherical hinge base of the affected side adjusting support is provided with a mechanical interface to facilitate the rapid butt-joint of the clamping device of the present disclosure and the tail end of the pelvic fracture robot. The clamping device disclosed by the present disclosure has remarkable advantages of compact structure, flexible adjustment, active variable stiffness, stable clamping, and convenient assembly and disassembly.

Figure 1:
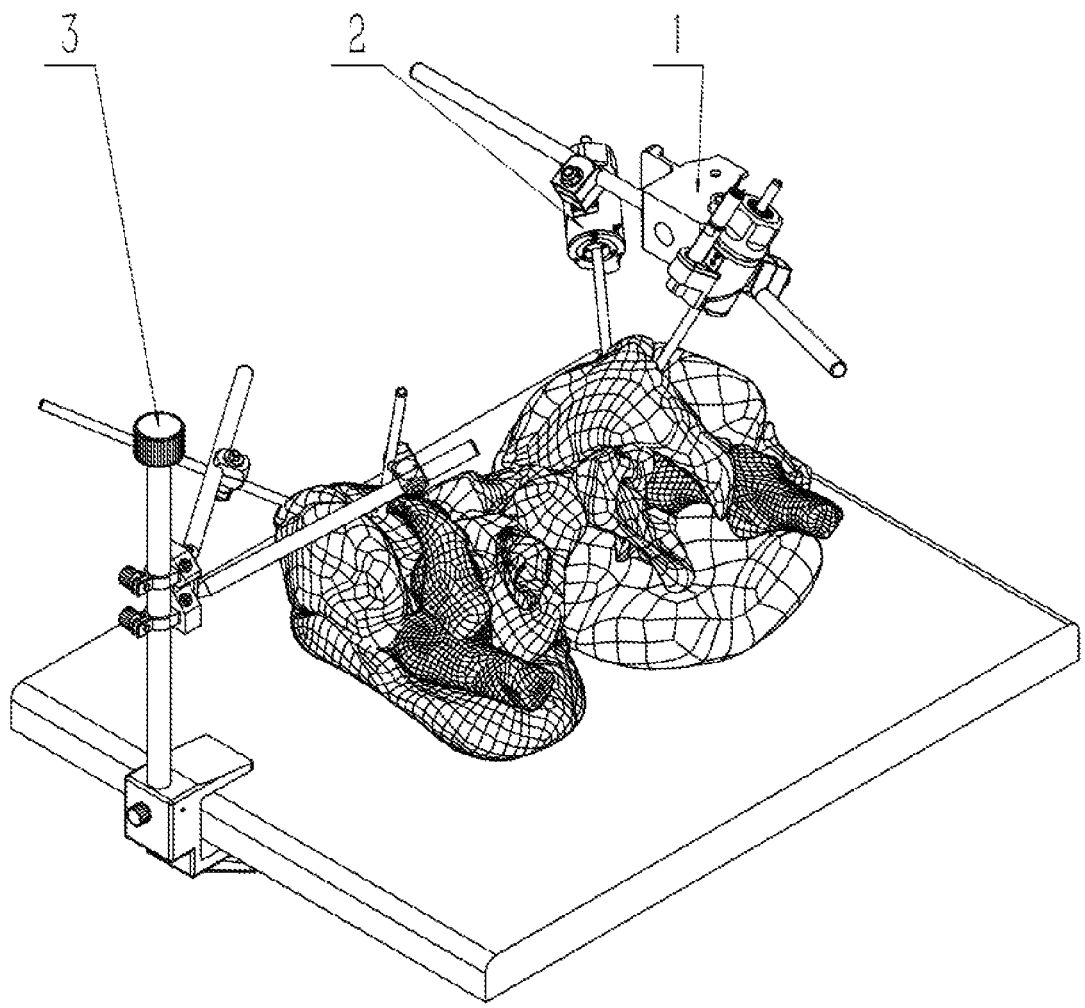
FIG. 1 is a schematic diagram of a structure under an initial state of the present disclosure in an embodiment 1.

In the drawings: 1—affected side adjusting support module; 2—electric pin rod connector module; 3—healthy side fixing module; 11—affected side cross rod; 12—affected side spherical hinge base; 13—affected side spherical hinge stop pin; 14—affected side spherical hinge stopper; 15—affected side spherical hinge; 16—affected side spherical hinge cover plate; 17—affected side spherical hinge cross rod; 18—affected side adjuster; 21—pin clamping assembly; 22—gasket stud; 23—cross rod clamping assembly; 211—nut; 212—elastic collet; 213—gear motor; 214—first-stage cylinder; 215—gear; 216—inner cylinder holder; 217—second-stage cylinder; 218—ball bushing; 219—third-stage cylinder; 2110—gearbox casing; 2111—first-stage spiral hole; 2112—inner cylinder boss; 2113—inner cylinder straight groove; 2114—second-stage adjusting boss; 2115—second-stage spiral hole; 2116—adjusting gear teeth; 2117—third-stage adjusting boss; 30—healthy side fixers; 31—healthy side bed clamp rotary knob; 32—healthy side bed clamp gasket; 33—healthy side bed clamp seat; 34—healthy side support rod rotary knob; 35—healthy side support rod; 36—healthy side spherical hinge base; 37—healthy side spherical hinge base fixing rotary knob; 38—healthy side spherical hinge stop pin; 39—healthy side spherical hinge cover plate; 310—healthy side spherical hinge cross rod; 311—pin rod connector; 312—healthy side pin.

DETAILED DESCRIPTION OF THE EMBODIMENTS

The following further describes the present disclosure in detail through specific embodiments, but is not intended to limit the scope of the present disclosure.

Embodiment 1

Figure 2:
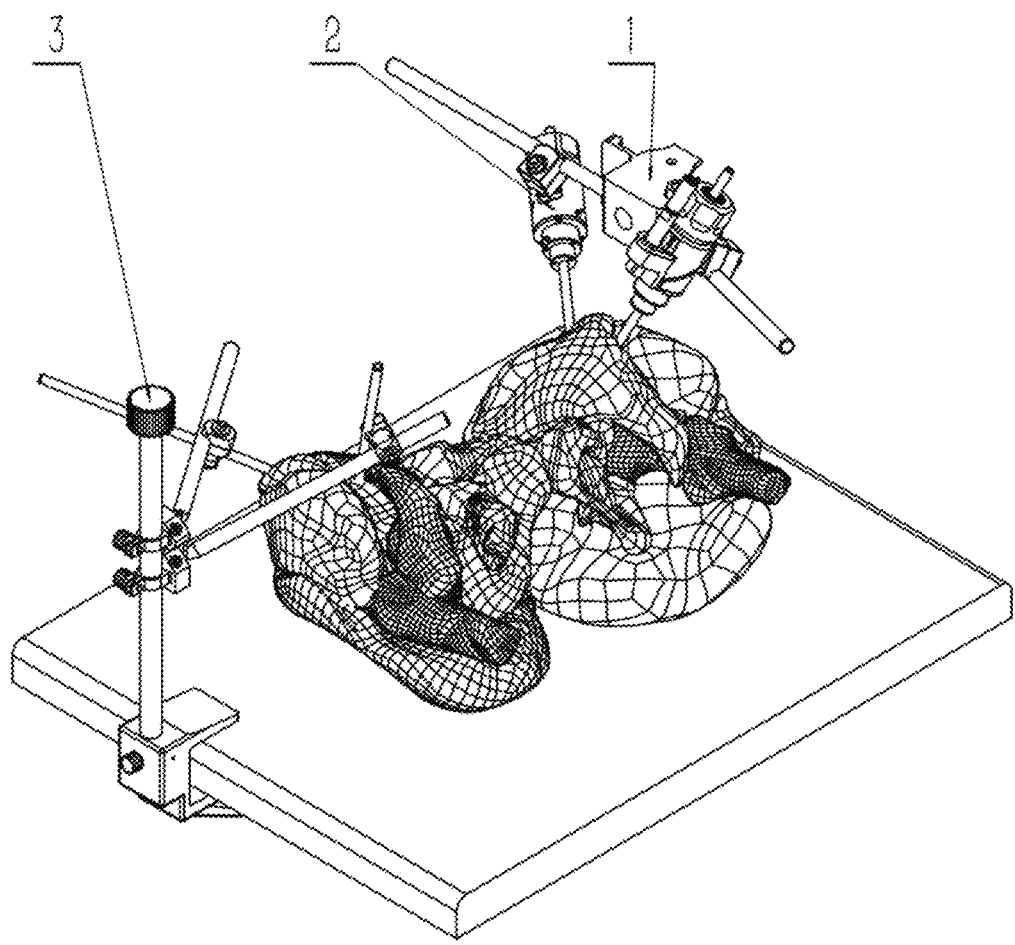
FIG. 2 is a schematic diagram of a structure under an elongation state of the present disclosure in an embodiment 1.
Figure 3:
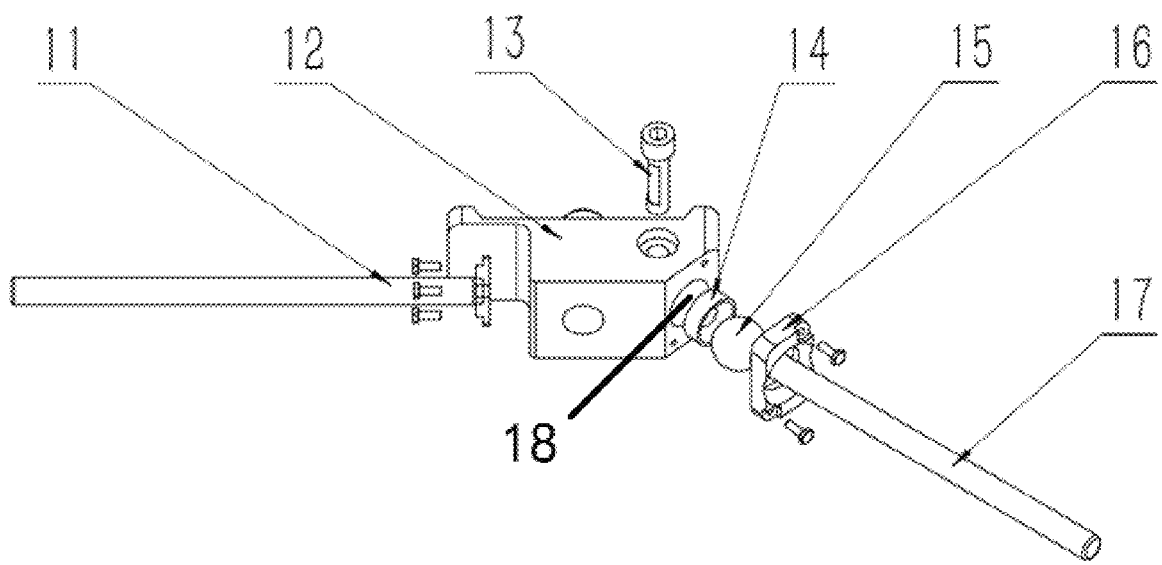
FIG. 3 is a schematic diagram of a structure of an affected side adjusting support module in an embodiment 1.
Figure 4:
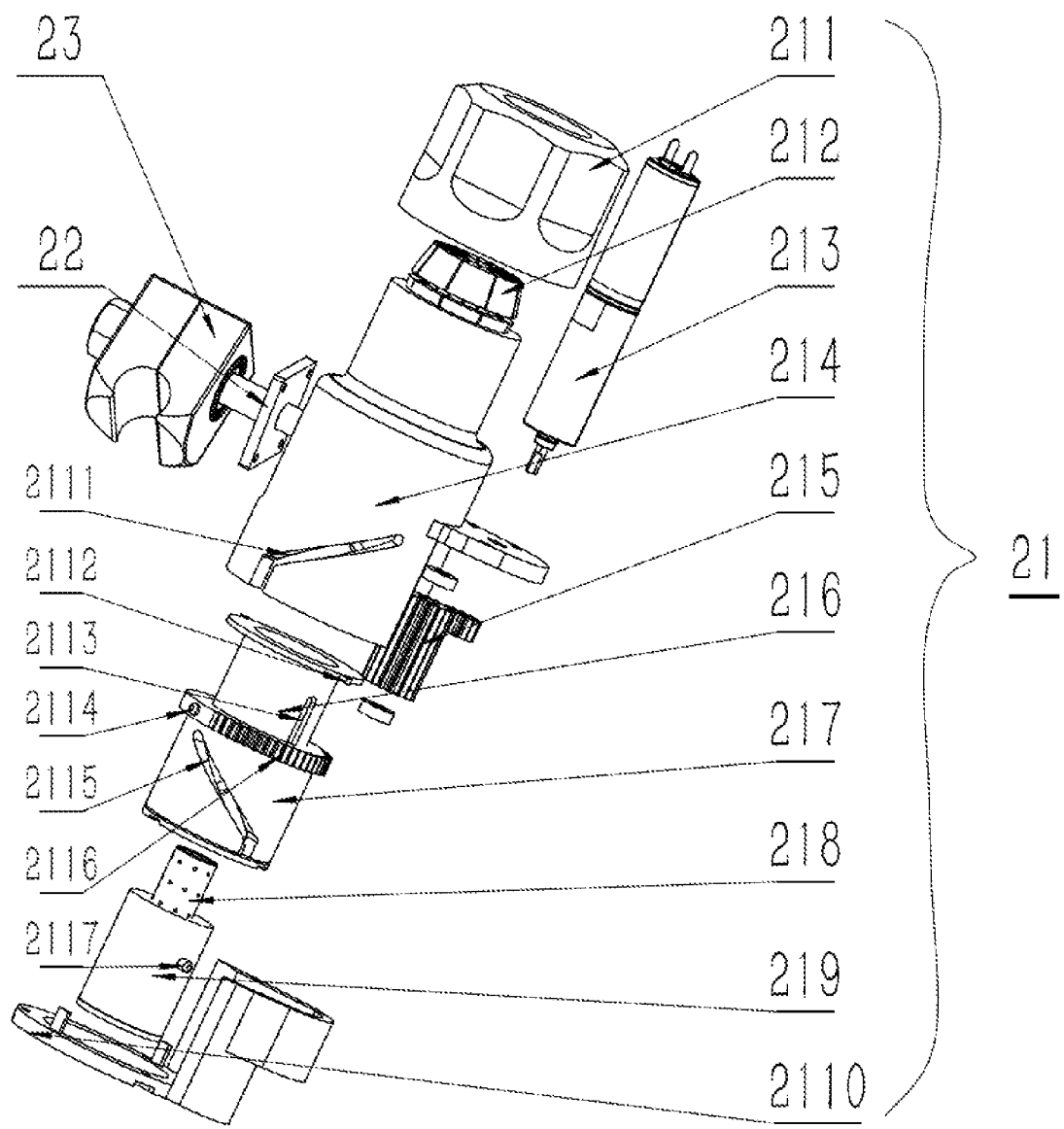
FIG. 4 is a schematic diagram of a structure of an electric pin rod connector in an embodiment 1.
Figure 5:
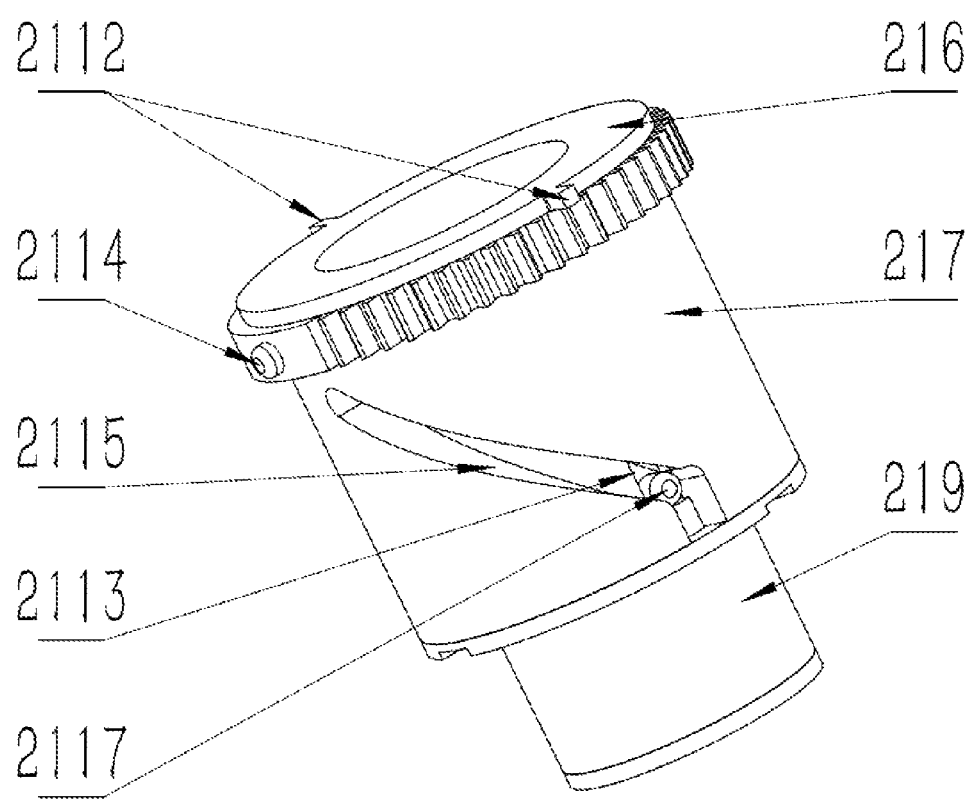
FIG. 5 is a schematic diagram of a structure of a telescopic part of an electric pin rod connector in an embodiment 1.
Figure 6:
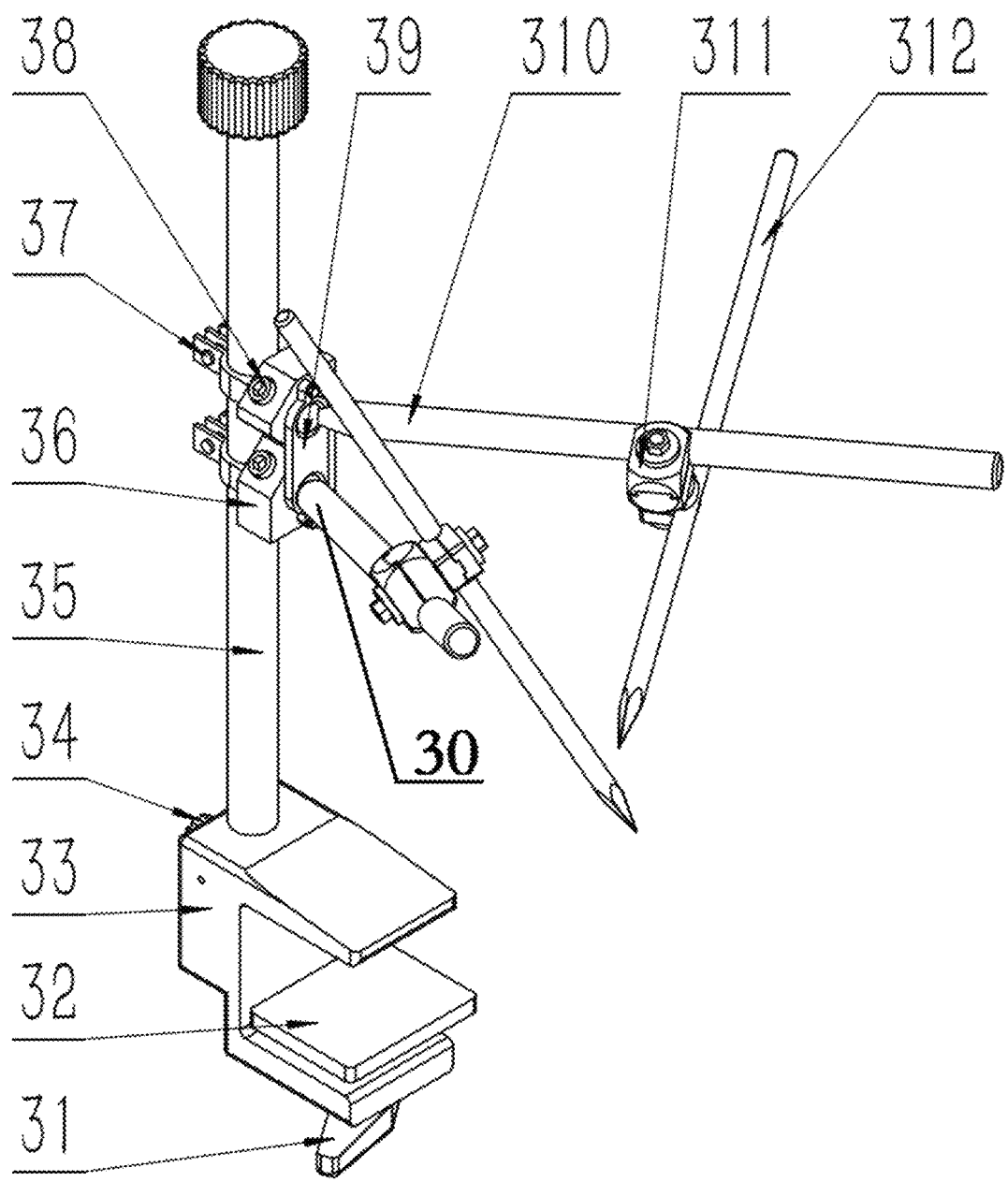
FIG. 6 is a schematic diagram of a structure of a healthy side fixing module in an embodiment 1.

An active variable stiffness clamping device for pelvic fracture reduction robot, as shown in FIG. 1 to FIG. 6, includes an affected side adjusting support module 1 and a healthy side fixing module 3 which are in fit with each other. The affected side adjusting support module 1 is provided with a pair of electric pin rod connector modules 2 connected to the affected side adjusting support module 1. The healthy side fixing module 3 includes a healthy side bed clamp seat 33, the healthy side bed clamp seat 33 is provided with a healthy side support rod 35, the healthy side support rod 35 is provided with a healthy side spherical hinge base 36, and the healthy side spherical hinge base 36 is provided with a pair of healthy side fixers 30 which are in clearance fit with each other.

The affected side adjusting support module 1 includes an affected side spherical hinge base 12. The affected side spherical hinge base 12 is provided with an affected side cross rod 11 and an affected side spherical hinge cross rod 17 which are in clearance fit with each other. The affected side cross rod 11 is fixedly connected to the affected side spherical hinge base 12, and the affected side spherical hinge cross rod 17 is connected to the affected side spherical hinge base 12 by an affected side adjuster 18.

The affected side adjuster 18 includes an affected side spherical hinge hole arranged on the affected side spherical hinge base 12, and the affected side spherical hinge hole is in fit with an affected side spherical hinge 15 arranged at the end part of the affected side spherical hinge cross rod 17. The affected side spherical hinge base 12 is provided with an affected side spherical hinge cover plate 16, and an affected side spherical hinge stopper 14 in fit with the affected side spherical hinge cross rod 17 is nested in the affected side spherical hinge cover plate 16. The affected side spherical hinge base 12 is provided with an affected side spherical hinge stop pin 13, the affected side spherical hinge stop pin 13 is in fit with the affected side spherical hinge 15 through an affected side limit hole which is formed in the affected side spherical hinge base 12 to communicate with the affected side spherical hinge hole.

The electric pin rod connector module 2 includes a cross rod clamping assembly 23 respectively connected to the affected side cross rod 11 and the affected side spherical hinge cross rod 17. A pin clamping assembly 21 is connected to the cross rod clamping assembly 23 by a gasket stud 22. The pin clamping assembly 21 includes a first-stage cylinder 214 connected to the gasket stud 22, the top end of the first-stage cylinder 214 is provided with an elastic collet 212, and the elastic collet 212 is provided with a nut 211 threaded to the elastic collet 212.

A second-stage cylinder 217 in clearance fit with the first-stage cylinder 214 is nested in the first-stage cylinder 214, an inner cylinder holder 216 is arranged at the top end of the second-stage cylinder 217, and the inner cylinder holder 216 is in fit with a straight groove in the first-stage cylinder 214. A third-stage cylinder 219 in clearance fit with the first-stage cylinder 214 is nested in the second-stage cylinder 217.

The second-stage cylinder 217 is provided with a second-stage adjusting boss 2114, the second-stage adjusting boss 2114 is in fit with a first-stage spiral hole 2111 on the first-stage cylinder 214. The first-stage cylinder 214 is provided with a gear motor 213, the movable end of the gear motor 213 is provided with a gear 215, the gear 215 is meshed with adjusting gear teeth 2116 arranged on the second-stage cylinder 217, and the adjusting gear teeth 2116 are in clearance fit with the inner surface of the first-stage cylinder 214.

The second-stage cylinder 217 is provided with a second-stage spiral hole 2115, the second-stage spiral hole 2115 is in fit with a third-stage adjusting boss 2117 arranged on the third-stage cylinder 219. An affected side pin in clearance fit with the second-stage cylinder 217 and the third-state cylinder 219 is nested in the first-stage cylinder 214; the affected side pin is in running fit with a ball bushing 218 nested in the third-stage cylinder 219, and the top end of the affected side pin is in fit with the elastic collet 121. An inner cylinder straight groove 2113 in fit with the third-stage adjusting boss 2117 is arranged on the inner cylinder holder 216. The first-stage cylinder 214 is provided with a gearbox casing 2110 in fit with the gear 215.

The healthy side fixers 30 each include a healthy side spherical hinge cross rod 210 hinged to a healthy side spherical hinge base 316, the healthy side spherical hinge cross rod 310 is provided with a pin rod connector 311 adjustably connected to the healthy side spherical hinge cross rod 310, and the pin rod connector 311 is provided with a healthy side pin 312 adjustably connected to the pin rod connector 311. The healthy side bed clamp seat 33 is provided with a healthy side support rod rotary knob 34 in fit with the healthy side support rod 35, the healthy side bed clamp seat 33 is provided with a healthy side bed clamp rotary knob 31, the healthy side bed clamp rotary knob 31 is in fit with a healthy side bed clamp groove arranged on the healthy side bed clamp seat 33 through a healthy side bed clamp gasket 32. One side, away from the healthy side spherical hinge cross rod 310, of the healthy side spherical hinge base 36 is provided with a healthy side spherical hinge base fixing rotary knob 37 in fit with the healthy side support rod 35, and one side, close to the healthy side spherical hinge cross rod 310, of the healthy side spherical hinge base is provided with a healthy side spherical hinge cover plate 39 in fit with the healthy side spherical hinge cross rod 310. The healthy side spherical hinge base 36 is provided with a healthy side spherical hinge stop pin 38 in fit with the healthy side spherical hinge cross rod 310.

The working principle of the present disclosure is as follows:

(1) The affected side pin and the healthy side pin 312 are respectively placed in the affected side ala of ilium and healthy side ala of ilium of the injured pelvis.

(2) The healthy side bed clamp seat 33 is connected to the healthy side support rod 35, the healthy side bed clamp rotary knob 31 is rotated to drive the healthy side bed clamp gasket 32 to fix the healthy side bed clamp seat 33, and thus the healthy side bed clamp seat 33 is fixed to one side of an operation table. The healthy side support rod 35 is rotated to an appropriate angle, the healthy side support rod rotary knob 34 is turned to a position for fixing the healthy side support rod 35. The healthy side spherical hinge base 36 is adjusted to an appropriate height, and the healthy side spherical hinge base 36 is fixed by the healthy side spherical base fixing rotary knob 37. The healthy side pin 312 is connected to the healthy side spherical hinge cross rod 310 by the pin rod connector 311, the healthy side spherical hinge cross rod 310 is locked by adjusting the healthy side spherical hinge stop pin 38, the healthy side spherical hinge cover plate 39 is configured to protect the healthy side spherical hinge cross rod 310, and the degree of firmness at each part of the healthy side fixing module 3 is screwed and checked.

(3) An angle between the affected side spherical hinge cross rod 17 and the affected side spherical hinge base 12 in the affected side adjusting support module 1 is adjusted, the affected side spherical hinge 15 rotates in the affected side spherical hinge hole, the affected side spherical hinge cover plate 16 is in fit with the affected side spherical hinge stopper 14 to protect the affected side spherical hinge cross rod 17; and after the angle of the affected side spherical hinge cross rod 17 is adjusted, the affected side spherical hinge stop pin 13 is configured to fix and limit the affected side spherical hinge 15 through the affected side limit hole. The affected side pin placed in the affected side ala of ilium is connected to the affected side adjusting support module 1 by the electric pin rod connector module 2, with specific steps as follows: the pin clamping assembly 21 is configured to fix the affected side pin, the affected side pin enters the elastic collet 212 after passing through the third-stage cylinder 219, the ball bushing 218, the second-stage cylinder 217 and the first-stage cylinder 214 in sequence, the nut 211 is rotated to clamp the elastic collet 212 so as to fix and clamp the affected side pin. The first-stage cylinder 214 is connected to the cross rod clamping assembly 23 through the gasket stud 22, the cross rod clamping assembly 23 is rotationally adjusted around the axis of the gasket stud 22, and after being adjusted, the cross rod clamping assembly 23 is clamped to the affected side cross rod 11 and the affected side spherical hinge cross rod 17, respectively, the cross rod clamping assembly 23 is fixed by using the nut, and finally, the degree of firmness at each connecting part of the affected side adjusting support module 1 and the electric pin rod connector module 2 are screwed and checked.

When the affected side pin is subjected to active stiffness regulation and control through the electric pin rod connector modules 2, the gear motor 213 is meshed with the adjusting gear teeth 2116 through the gear 215, thus driving the second-stage cylinder 217 to rotate along with the gear 215. The inner cylinder holder 216 in the second-stage cylinder 217 is provided with the inner cylinder boss 2112, and the inner cylinder boss 2112 moves along a straight line of the straight groove in the first-stage cylinder 214. When the second-stage adjusting boss 2114 moves along the first-stage spiral hole 2111, the second-stage spiral hole 2115 rotates along with the second-stage cylinder 217, and at the moment, the inner cylinder holder 216 moves linearly along with the second-stage cylinder 217, and the inner cylinder straight groove 2113 moves along with the inner cylinder holder 216. The third-stage adjusting boss 2117 is in fit with the second-stage spiral hole 2115 and the inner cylinder straight groove 2113, and the third-stage cylinder 219 extends and retracts along a straight line when the second-stage cylinder 217 extends and retracts spirally. Therefore, the second-stage cylinder 217 and the third-stage cylinder 219 are driven by the gear motor 213 to extend and retract so as to achieve the active stiffness regulation of the affected side pin.

(4) After the pelvis is firmly fixed, the pelvic fracture robot is in rapid butt-joint with the mechanical interface of the affected side spherical hinge base 12 in the affected side adjusting support module 1, thus completing the connection between the clamping device and the pelvic fracture robot.

Embodiment 2

An active variable stiffness clamping device for pelvic fracture robot reduction is different from the embodiment 1 in that the affected side adjusting support module 1 includes an affected side spherical hinge base 12, the affected side spherical hinge base 12 is provided with a pair of affected side spherical hinge cross rods 17 in angle fit with each other. The affected side spherical hinge cross rods 17 are connected to the affected side spherical hinge base 12 by the affected side adjuster 18, and the affected side cross rods 11 are replaced with the affected side spherical hinge cross rods 17.

Embodiment 3

An active variable stiffness clamping device for pelvic fracture robot reduction is different from the embodiment 1 in that the affected side adjusting support module 1 includes an affected side spherical hinge base 12, the affected side spherical hinge base 12 is provided with a pair of affected side cross rods 11 in angle fit with each other. The affected side cross rods 11 are fixedly connected to the affected side spherical hinge base 12, and the affected side spherical hinge cross rods 17 are replaced with the affected side cross rods 11.

Embodiment 4

An active variable stiffness clamping device for pelvic fracture robot reduction is different from the embodiment 1 in that an included angle between the affected side cross rod and the affected side spherical hinge cross rod is a, $0° \leq \alpha \leq 135°$, where the a may be one of 0°, 15°, 30°, 45°, 60°, 75°, 90°, 105°, 120°, 135°.

The above is only a preferred embodiment of the present disclosure, but it is not limited to the above examples. Any modification, equivalent substitution and improvement made within the spirit and principle of the present disclosure should fall within the scope of protection of the present disclosure.

What is claimed is:

1. An active variable stiffness clamping device for pelvic fracture reduction robot, comprising an affected side adjusting support module and a healthy side fixing module which are in fit with each other, wherein the affected side adjusting support module is provided with a pair of electric pin rod connector modules connected to the affected side adjusting support module; the healthy side fixing module comprises a healthy side bed clamp seat, the healthy side bed clamp seat is provided with a healthy side support rod, the healthy side support rod is provided with a healthy side spherical hinge base, and the healthy side spherical hinge base is provided with a pair of healthy side fixers which are in clearance fit with each other, wherein the affected side adjusting support module comprises an affected side spherical hinge base; the affected side spherical hinge base is provided with an affected side cross rod and an affected side spherical hinge cross rod which are in clearance fit; the affected side cross rod is fixedly connected to the affected side spherical hinge base, and the affected side spherical hinge cross rod is connected to the affected side spherical hinge base by an affected side adjuster, and wherein the affected side adjuster comprises an affected side spherical hinge hole arranged on the affected side spherical hinge base, the affected side spherical hinge hole is in fit with an affected side spherical hinge arranged at the end part of the affected side spherical hinge cross rod; the affected side spherical hinge base is provided with an affected side spherical hinge cover plate, and an affected side spherical hinge stopper in fit with the affected side spherical hinge cross rod is nested in the affected side spherical hinge cover plate; the affected side spherical hinge base is provided with an affected side spherical hinge stop pin, and the affected side spherical hinge stop pin is in fit with the affected side spherical hinge through an affected side limit hole which is formed in the affected side spherical hinge base to communicate with the affected side spherical hinge hole.

2. The active variable stiffness clamping device for pelvic fracture reduction robot according to claim 1, wherein the electric pin rod connector module comprises a cross rod clamping assembly respectively connected to the affected side cross rod and the affected side spherical hinge cross rod; a pin clamping assembly is connected to the cross rod clamping assembly by a gasket stud; the pin clamping assembly comprises a first-stage cylinder connected to the gasket stud, a top end of the first-stage cylinder is provided with an elastic collet, and the elastic collet is provided with a nut threaded to the elastic collet.

3. The active variable stiffness clamping device for pelvic fracture reduction robot according to claim 2, wherein a second-stage cylinder in clearance fit with the first-stage cylinder is nested in the first-stage cylinder, an inner cylinder holder is nested in the second-stage cylinder, and the inner cylinder holder is in fit with a straight groove in the first-stage cylinder; and a third-stage cylinder in clearance fit with the first-stage cylinder is nested in the second-stage cylinder.

4. The active variable stiffness clamping device for pelvic fracture reduction robot according to claim 3, wherein the second-stage cylinder is provided with a second-stage adjusting boss, the second-stage adjusting boss is in fit with a first-stage spiral hole on the first-stage cylinder; the first-stage cylinder is provided with a gear motor, a movable end of the gear motor is provided with a gear, the gear is meshed with adjusting gear teeth arranged on the second-stage cylinder, and the adjusting gear teeth are in clearance fit with the inner surface of the first-stage cylinder.

5. The active variable stiffness clamping device for pelvic fracture reduction robot according to claim 4, wherein the second-stage cylinder is provided with a second-stage spiral hole, the second-stage spiral hole is in fit with a third-stage adjusting boss arranged on the third-stage cylinder, an affected side pin in clearance fit with the second-stage cylinder and the third-state cylinder is nested in the first-stage cylinder, the affected side pin is in running fit with a ball bushing nested in the third-stage cylinder, and the top end of the affected side pin is in fit with the elastic collet; an inner cylinder straight groove in fit with the third-stage adjusting boss is arranged on the inner cylinder holder; and the first-stage cylinder is provided with a gearbox casing in fit with the gear.

6. The active variable stiffness clamping device for pelvic fracture reduction robot according to claim 5, wherein the healthy side fixers each comprise a healthy side spherical hinge cross rod hinged to a healthy side spherical hinge base, the healthy side spherical hinge cross rod is provided with a pin rod connector adjustably connected to the healthy side spherical hinge cross rod, and the pin rod connector is provided with a healthy side pin adjustably connected to the pin rod connector.

7. The active variable stiffness clamping device for pelvic fracture reduction robot according to claim 6, wherein the healthy side bed clamp seat is provided with a healthy side support rod rotary knob in fit with the healthy side support rod, the healthy side bed clamp seat is provided with a healthy side bed clamp rotary knob, and the healthy side bed clamp rotary knob is in fit with a healthy side bed clamp groove arranged on the healthy side bed clamp seat through a healthy side bed clamp gasket.

8. The active variable stiffness clamping device for pelvic fracture reduction robot according to claim 7, wherein one side, away from the healthy side spherical hinge cross rod, of the healthy side spherical hinge base is provided with a healthy side spherical hinge base fixing rotary knob in fit with the healthy side support rod, and one side, close to the healthy side spherical hinge cross rod, of the healthy side spherical hinge base is provided with a healthy side spherical hinge cover plate in fit with the healthy side spherical hinge cross rod; and the healthy side spherical hinge base is provided with a healthy side spherical hinge stop pin in fit with the healthy side spherical hinge cross rod.

9. The active variable stiffness clamping device for pelvic fracture reduction robot according to claim 1, wherein the healthy side fixers each comprise a healthy side spherical hinge cross rod hinged to a healthy side spherical hinge base, the healthy side spherical hinge cross rod is provided with a pin rod connector adjustably connected to the healthy side spherical hinge cross rod, and the pin rod connector is provided with a healthy side pin adjustably connected to the pin rod connector.

10. The active variable stiffness clamping device for pelvic fracture reduction robot according to claim 9, wherein the healthy side bed clamp seat is provided with a healthy side support rod rotary knob in fit with the healthy side support rod, the healthy side bed clamp seat is provided with a healthy side bed clamp rotary knob, and the healthy side bed clamp rotary knob is in fit with a healthy side bed clamp groove arranged on the healthy side bed clamp seat through a healthy side bed clamp gasket.

11. The active variable stiffness clamping device for pelvic fracture reduction robot according to claim 10, wherein one side, away from the healthy side spherical hinge cross rod, of the healthy side spherical hinge base is provided with a healthy side spherical hinge base fixing rotary knob in fit with the healthy side support rod, and one side, close to the healthy side spherical hinge cross rod, of the healthy side spherical hinge base is provided with a healthy side spherical hinge cover plate in fit with the healthy side spherical hinge cross rod; and the healthy side spherical hinge base is provided with a healthy side spherical hinge stop pin in fit with the healthy side spherical hinge cross rod.

\* \* \* \* \*